United States Patent
Khanuja et al.

(10) Patent No.: US 7,435,433 B2
(45) Date of Patent: Oct. 14, 2008

(54) PROCESS FOR THE ISOLATION OF OLEANE COMPOUNDS ISOLATED FROM THE BARK OF ARJUN TREE TERMINALIA ARJUNA (ROXB.)

(75) Inventors: Suman Preet Singh Khanuja, Lucknow (IN); Madan Mohan Gupta, Lucknow (IN); Santosh Kumar Srivastava, Lucknow (IN); Tiruppadiripuliyur Ranganathan Santha Kumar, Bronx, NY (US); Digvijay Singh, Lucknow (IN); Subash Chandra Verma, Lucknow (IN); Ankur Grag, Lucknow (IN); Merajuddin Khan, Lucknow (IN); Ram Kishor Verma, Lucknow (IN); Raghavendra Kumar Mishra, Lucknow (IN); Subash Chandra Singh, Lucknow (IN)

(73) Assignee: Council of Scientific & Industrial Research, New Deli (IN)

( * ) Notice: Subject to any disclaimer, the term of this patent is extended or adjusted under 35 U.S.C. 154(b) by 0 days.

(21) Appl. No.: 11/395,734

(22) Filed: Mar. 31, 2006

(65) Prior Publication Data
US 2007/0122506 A1 May 31, 2007

(30) Foreign Application Priority Data
Nov. 25, 2005 (IN) .................. 3160/DEL/2005

(51) Int. Cl.
*A61K 36/00* (2006.01)
(52) U.S. Cl. ....................... 424/775; 424/725
(58) Field of Classification Search ............... None
See application file for complete search history.

(56) References Cited

U.S. PATENT DOCUMENTS 4,103,025 A * 7/1978 Mustich ............... 514/548

OTHER PUBLICATIONS

Singh et al., "Arjunetin from *Terminalia arjuna* as an insect feeding-deterrent and growth inhibitor" (2004), Phytotherapy Research, vol. 18, Issue 2, pp. 131-134.*
Pelletier et al., "Separation of diterpenoid alkaloid mixtures using vacuum liquid chrmoatography" (1986), Journal of Natural Products, vol. 49 (5), pp. 892-900.*

* cited by examiner

*Primary Examiner*—Christopher R. Tate
(74) *Attorney, Agent, or Firm*—Dickinson Wright PLLC

(57) ABSTRACT

The present invention provides an improved process for the isolation of oleane compounds from the bark of *Terminalia arjuna* (Roxb.). More particularly, the present invention relates to an improved process for the isolation of arjunic acid and its derivates from the bark of *Terminalia arjuna* (Roxb.). The present invention further provides the identification of arjunic acid [1] and its derivatives as anticancer agent useful in the treatment of various types of cancer in humans.

9 Claims, No Drawings

PROCESS FOR THE ISOLATION OF OLEANE COMPOUNDS ISOLATED FROM THE BARK OF ARJUN TREE TERMINALIA ARJUNA (ROXB.)

FIELD OF INVENTION

The present invention relates to an improved process for the isolation of oleane compounds from the bark of *Terminalia arjuna* (Roxb.). More particularly, the present invention relates to an improved process for the isolation of arjunic acid and its derivates from the bark of *Terminalia arjuna* (Roxb.).

BACKGROUND OF INVENTION

Arjunic acid ($2\pm,3^2,19\pm$-tri-hydroxy-olea-12-en-28-oic acid) (1) is a triterpenoid compound which exists widely in natural plants in the form of free acid or aglycone for triterpenoid saponins, it has been isolated and identified from various plant species.

The bark of arjun tree *Terminalia arjuna* has been extensively used in Indian Ayurvedic system of medicine, especially as a cardiac tonic. Vagbhatta mentioned the use of *Terminalia arjuna* for treating heart diseases about 1200 years ago [L. C. Vaidya, 1963 commentaries on Vagbhatta in "Asttong Hridyam" Motilal Banarsi Das, Varanasi, first edition: 414]. A decoction of its bark with cane sugar and boiled cows milk is highly recommended for endocarditis, pericarditis and angina (Kumar D S and Prabhakar Y S, *J. Ethanopharmacology*, 1987, 20, 173.). The bark is also prescribed in biliousness and sores and as antidote to poison and it is believed to have an ability to cure hepatic congenital, veneral and viral disease.

Habit: *Terminalia arjuna* tree is distributed throughout the greater part of India, Burma, and Sri Lanka, wherever plenty of water is available. It is practically found in sub-Himalayan tracks of Uttar Pradesh, South Bihar, Madhya Pradesh and Deccan regions. The trees are also being grown in the road side of big cities as an ornamental tree and they grow well whenever there is collection or flow of water in the neighborhood.

Chemical investigation: Significant work on the chemical investigation of different parts of *Terminalia arjuna* resulted in the isolation and characterization of number of compounds as given below in Table-1

TABLE 1

Phytochemical constituents of various parts of *Terminallia arjuna*

| Parts | Chemical constituents |
| --- | --- |
| Stem bark | Alkaloids, Tannins, Sugars, Coloring matter, $^2$-Sitosterol, Ellagic acid, CaO, MgO, $Al_2O_3$, Arjunolic acid, Arjunic acid (arjunin), Friedlin, Arjunentin, Leucocyanidin, Adrjungenin, Arjunoglucoside-I, Arjunoglucoside-II, Arjunoglucoside-III, Arjunolitin, Arjunolone, Oxalic acid, (+)Catechol, Baicalein, Luteolin, Terminic acid, Flavonoids, |
| Root bark | Ellagic acid, Gallic acid, Arjunatin, leucocyanidin, Arjunoglucoside-I, Arjunoside-II, Arjunoside-III, Arjunoside-IV, Terminic acid, $^2$-hydroxyhexadecanoic acid. |
| Fruits | Tannin, Ellagic acid, Gallic acid, Xylan, Mannitol, KCl, Sitosterol, Sitosterolglucoside, Afxormosin, Quercitin-7-Orhamnoside, Arjunic acid, Arjunone, Cerasidin, Methyl-oleanorate, Hentriacontone, Arachidic sterate, Myristyloleate, Triterpeneglycoside (Terminolitin), Hentriacontane. |

TABLE 1-continued

Phytochemical constituents of various parts of *Terminallia arjuna*

| Parts | Chemical constituents |
| --- | --- |

Biological activities: Pettit et al have examined, the cancer cell growth inhibitory constituents residing in the bark, stem, leaves of the Marutious medicinal plant *T. arjuna* by means of bioassay-guided separation method. The cancer line active components were found to be gallic acid, ethyl gallate flavone, leutonolin. Luteolin has a well established record of inhibiting various cancer cell lines and may account for the most of the rationale underlying the use of *T. arjuna* in traditional cancer treatment. Luteolin was also found to exhibit specific activity against the pathogenic bacteria *Neisseria gonorrhoeae* [G R Pettit, M S Hoard, D L Doubek, J M Schmidt, R K Pettit, L P Tackett, J C Chapuis, 1996, *J Ethnopharmacology*, 53, 57]. Kaur et al reported the antimutagenic potential of a fraction isolated from *T. arjuna*, evaluated in TA98 and TA100 strains of *salmonella typhimurium* against direct and indirect acting mutagens. The fraction was quit effective against 59-dependent 2AF while it showed moderate effect against NPD. The fraction was finally identified as Ellagic acid (S J Kaur, I S Grover, S Kumar, 1997, *Ind J Exp Biol*, 35, 478). Kandil et al have isolated a new ellagitanin named, Arjunin along with four known tannins and two phenolic acids from *T. arjuna*. The biological activity examination of the ethnolic extract of the leaves of *T. arjuna* and isolated compound Arjunin showed that they have moderate cytotoxic activity against BT-20 human breast carcinoma cells. The $IC_{50}$ of the extract and the compound Arjunin were 2.5 and 6.5 mg/ml, respectively. The growth inhibition effect of compound Arjunin was higher than that of the extract (F E Kandil, I N Mahmood, 1998, *Phytochemistry*, 47, 1567.)

Chaturvedi et al. reported that the alcoholic extract of *T. arjuna* has statistically significant hypocholesterolemic, hypolipidemic, anticoagulant and fibrinolytic effect on hypercholesterolemic rabbits. It also shows no definite action on the serum phospholipids. The alcoholic extract has no protective action against isoprenaline induced experimental myocardial injury. Pharmacological investigations show "*arjuna*" has cardiotonic property in animals. They concluded that it may be safely used for the prevention and treatment of the patients of ischaemic heart diseases [G. N. Chaturvedi. 1973. *Studies on ischaemic_heart diseases and its management by indegenious drugs*, Ph.D. Thesis, Dept. of Kayachikitsa I.M.S., B.H.U., varanasi].

Pathak et al. reported that *T. arjuna* bark powder in the dose of 20 mg/100 gm body weight shows a significant reduction in plasma cholesterol, plasma catecholamine along with lowering in plasma protein and brain catecholamine in the infarcted rats. Their study suggests the importance of this drug as a possible remedy in myocardial infarction as it was shown to be hypocholesteremic, anticatecholaminic and possibly an inhibitor of catecholamine release from the adrenal glands [S. R. Pathak, R. H. Singh, K. N. Udupa. 1987. *Alter. Med.* 2: 203].

It was observed that although arjunic acid has been isolated earlier by some other workers, due to the poor yield and tedious column chromatographic separation procedures of the anticancer agent from the bark of *T. arjuna* this bioactive constituent will become an expensive pharmaceutical compound. This prompted us to develop an inexpensive, easy and economical isolation process for this important anticancer agent so that it can be brought within reach of the common masses.

On going through the literature, it was observed that arjunic acid was isolated from the bark of *T. arjuna* in ~0.025% yield (Row L R et al, 1970, *Ind J Chem*, 8, 716-721). This process involved successive extraction of powdered *T. arjuna* bark with petroleum ether, ether and ethanol in a large Soxhlet extractor. The ether extract during removal of solvent yielded a crystalline powder, which was dissolved in acetic acid and filtered. The filtrate on dilution with water gave a solid, which on crystallization with MeOH afforded arjunic acid in ~0.025% yield.

The method described above suffers from a number of disadvantages. The biggest disadvantage is the low yield of arjunic acid. The second disadvantage of the above process is that the total solid is being dissolved in acetic acid. Since arjunic acid itself is an acid, hence it would have not been dissolved completely in acetic acid, which may be one of the reasons for the poor yield of arjunic acid in this process.

In 1986 Honda et al (*Bull. Chem. Soc. Japan*, 49, 3213-3218) reported isolation of arjunic acid from the bark of *T. arjuna* in 0.02% yield. The process involved cold extraction of powdered *T. arjuna* bark with MeOH followed by addition of lead acetate resulting in the precipitation of the material followed by filtration. To the filtrate further water was added to obtain more precipitate. The combined precipitates were further subjected to column chromatographic separation, which yielded arjunic acid in ~0.020% yield.

The method described above suffers from a number of disadvantages. The biggest disadvantage is the low yield of anticancer agent arjunic acid. The second disadvantage of the above process is that it utilizes a tedious column chromatographic method for separation of arjunic acid.

In 1982 Anjaneyulu and Rama Prasad (*Ind J Chem*, 21B, 530-533) reported the isolation of arjunic acid from the root bark of *T. arjuna* in ~0.015% yield. The isolation process involved successive extraction of powdered root bark of *T. arjuna* with n-hexane, chloroform, ethanol and EtOAc. The concentrated chloroform extract after maceration with hot ether gave arjunic acid in 0.015% yield.

The method described above suffers from a number of disadvantages. The biggest disadvantage is the poor yield of arjunic acid. The second disadvantage of the above process is that arjunic acid is being isolated from $CHCl_3$ extract of *T. arjuna* root bark, this may be the reason for poor yield of arjunic acid as it is not highly soluble in $CHCl_3$.

The method described above suffers from a number of disadvantages. The biggest disadvantage is the low yield of anticancer agent arjunic acid. The second disadvantage of the above process is that it utilizes a tedious column chromatographic method for the separation of arjunic acid.

OBJECTIVES OF THE INVENTION

The main object of the present invention is to provide an improved economical process for the isolation of arjunic acid from the bark of *T. arjuna*, which obviates the draw backs of the existing processes.

Another object of the present invention is to completely avoid the use of highly tedious, time taking column chromatographic purification process for the isolation of arjunic acid from the bark of *T. arjuna*.

Yet another object is the use of oleane compounds isolated from *Terminalia arjuna* as an anticancer agent against human cancer cell lines.

Still another object is the identification of arjunic acid [1] as an anticancer agent useful it the treatment of various types of human cancer such as colon, breast, liver and ovarian cancers.

SUMMARY OF THE INVENTION

Accordingly the present invention provides an improved process for the isolation of arjunic acid from the bark of *T. arjuna*, which comprises drying, grinding and defattening the *T. arjuna* bark in an organic solvent, followed by overnight extractions with a polar organic solvent, at a temperature in the range of 30-40° C. and removing the solvent, under vacuum, at a temperature in the range of 35-45° C. to obtain the crude arjunic acid rich fraction, dissolving the above said crude fraction in water and further extracting it with another organic solvent followed by the removal of solvent, under vacuum, at a temperature in the range of 35-45° C., washing the resultant crude so obtained with water and drying it by known methods and subjecting it to a Vacuum Liquid Chromatographic (VLC) process to obtain the desired pure arjunic acid.

In an embodiment of the present invention the organic solvent used for defattening the bark of *T. arjuna* is selected from the group consisting of petroleum spirit, hexane, benzene, toluene and dichloromethane.

In yet another embodiment the extraction of defattened *T. arjuna* bark is done at least three times with polar organic solvent.

In yet another embodiment the polar organic solvent used for the extraction of defattened *T. arjuna* bark is selected from the group consisting of dichloromethane, chloroform, ethyl acetate, ether, acetone, methanol, and ethanol.

In yet another embodiment the polar organic solvent used is methanol.

In yet another embodiment the organic solvent used for re-extraction of crude arjunic acid rich fraction is selected from the group consisting of dichloromethane, dichloroethane, chloroform, ethylacetate and diethyl.

In yet another embodiment the solvent used for re extraction is dichloroethane.

In yet another embodiment the gradient elution of vacuum liquid chromatographic (VLC) is carried out using a solvent selected from the group consisting of dichloromethane, dichloroethane, chloroform, ethylacetate, diethylether, acetone, methanol, ethanol, $H_2O$ and a mixture thereof.

In yet another embodiment the yield of arjunic acid obtained is in the range of 0.02-0.04%.

In yet another embodiment the arjunic acid obtained is biologically activity agent against human cancer disease.

In yet another embodiment the arjunic acid obtained is useful as anti cancer agent against but not limited to ovarian (PA-1), colon (Caco-2), breast (MCF-7) and liver (WRL-68) cancer cells.

The present invention further provides a pharmaceutical composition comprising arjunic acid or its derivatives, salts or mixture thereof isolated from the Genus *Terminalia arjuna* optionally with pharmaceutically acceptable carrier, adjuvants and additives.

In yet another embodiment the said composition is useful as biologically activity agent against human cancer disease.

In yet another embodiment the derivative of arjunic acid used is selected from the group consisting of arjunetin, arjungenin, arjunglucoside-I, Arjunic acid methyl ester, 2,3-Di-O-acetyl arjunic acid, 2,3-Di-O-acetyl arjunic acid methyl ester, 2,3-Di-O-ethyl arjunic acid methyl ester, 2,3-Di-O-benzoyl arjunic acid methyl ester, 2,3-Di-O-(o)-anisoyl arjunic acid methyl ester, 2,3-Di-O-(m)-anisoyl arjunic acid methyl ester, 2,3-Di-O-(p)-anisoyl arjunic acid methyl ester, 2,3-Di-O-crotonoyl arjunic acid methyl ester, 2,3-Di-O-palmitoyl arjunic acid methyl ester, 2,3-Di-O-myristoyl arjunic acid methyl ester and 2,3-Di-O-cinnamoyl arjunic acid methyl ester.

In yet another embodiment, the said composition is useful as anti cancer agent against but not limited to ovarian (PA-1), colon (Caco-2), breast (MCF-7) and liver (WRL-68) cancer cells.

In yet another embodiment the concentration of arjunic acid used in vitro MTT assay for IC 90 in cancer cell line MCF-7 of breast cancer is in the range of 4 to 60 μg/ml.

In yet another embodiment the concentration of arjunic acid used in vitro MTT assay for IC 90 in cancer cell line MCF-7 of breast cancer, WRL-68 of liver cancer, caco-2 of colon cancer and PA-1 of ovary cancer is in the range of 4 to 60 μg/ml.

In yet another embodiment the concentration of arjungenin used in vitro MTT assay for IC 90 in cancer cell line MCF-7 of breast cancer, caco-2 of colon cancer and PA-1 of ovary cancer is in the range of 50 to 60 μg/ml.

In yet another embodiment the concentration of arjunetin used in vitro MTT assay for IC 90 in cancer cell line MCF-7 of breast cancer, WRL-68 of liver cancer and caco-2 of colon cancer is in the range of 10 to 60 μg/ml.

In yet another embodiment the concentration of arjunglucoside-1 used in vitro MTT assay for IC 90 in cancer cell line caco-2 of colon cancer and PA-1 of ovary cancer is in the range of 10 to 60 μg/ml.

The present invention provides a use of pharmaceutical composition comprising arjunic acid or its derivatives, salts or mixture thereof isolated from the Genus *Terminalia arjuna* optionally with pharmaceutically acceptable carrier as an biologically activity agent against human cancer disease.

In yet another embodiment the composition is active against but not limited to ovarian (PA-1), colon (Caco-2), breast (MCF-7) and liver (WRL-68) cancer cells.

In yet another embodiment the concentration of arjunic acid used in vitro MTT assay for IC 90 in cancer cell line MCF-7 of breast cancer is in the range of 4 to 60 μg/ml.

In yet another embodiment the concentration of arjunic acid used in vitro MTT assay for IC 90 in cancer cell line MCF-7 of breast cancer, WRL-68 of liver cancer, caco-2 of colon cancer and PA-1 of ovary cancer is in the range of 4 to 60 μg/ml.

In yet another embodiment the concentration of arjungenin used in vitro MTT assay for IC 90 in cancer cell line MCF-7 of breast cancer, caco-2 of colon cancer and PA-1 of ovary cancer is in the range of 50 to 60 μg/ml.

In yet another embodiment the concentration of arjunetin used in vitro MTT assay for IC 90 in cancer cell line MCF-7 of breast cancer, WRL-68 of liver cancer and caco-2 of colon cancer is in the range of 10 to 60 μg/ml.

In yet another embodiment the concentration of arjunglucoside-1 used in vitro MTT assay for IC 90 in cancer cell line caco-2 of colon cancer and PA-1 of ovary cancer is in the range of 10 to 60 μg/ml.

In still another embodiment the derivative of arjunic acid used is selected from the group consisting of arjunetin, arjungenin, arjunglucoside-I, Arjunic acid methyl ester, 2,3-Di-O-acetyl arjunic acid, 2,3-Di-O-acetyl arjunic acid methyl ester, 2,3-Di-O-ethyl arjunic acid methyl ester, 2,3-Di-O-benzoyl arjunic acid methyl ester, 2,3-Di-O-(o)-anisoyl arjunic acid methyl ester, 2,3-Di-O-(m)-anisoyl arjunic acid methyl ester, 2,3-Di-O-(p)-anisoy arjunic acid methyl ester, 2,3-Di-O-crotonoyl arjunic acid methyl ester, 2,3-Di-O-palmitoyl arjunic acid methyl ester, 2,3-Di-O-myristoyl arjunic acid methyl ester and 2,3-Di-O-cinnamoyl arjunic acid methyl ester.

The following examples are given by way of illustration of the present invention and should not be construed to limit the scope of present invention.

EXAMPLE-1

Collection of Plant Material and Extraction

The bark of *Terminalia arjuna* was collected from CIMAP medicinal plant conservatory, during the month of January, 1999, identified in the department of Botany and Pharmacognosy at CIMAP where a voucher specimen (NO.5867) is maintained.

EXAMPLE-2

The air dried powdered bark of *T. arjuna* (3 Kg) was successively extracted with hexane and methanol. The dried methanol extract was dissolved in water and fractionated with chloroform. The solvent was removed under vacuum at 40° C. and the crude was further subjected to Vacuum Liquid Chromatography (VLC), which afforded arjunic acid in 0.02% yield.

EXAMPLE-3

The air dried powdered bark of *T. arjuna* (4.0 Kg) was defatted with hexane in cold (thrice) at room temperature. The defatted material was then extracted with EtOH: H2O (90:10) two times overnight at room temperature. The solvent was removed under vacuum at 40° C. and the crude extract so obtained was further diluted with water and extracted with ethyl acetate. The ethyl acetate extract was washed with water and dried over $Na_2SO_4$. The ethyl acetate was removed completely under vacuum at 40° C. and the crude so obtained was subjected to column chromatographic separation, which resulted in the isolation of pure arjunic acid in 0.029% yield.

EXAMPLE-4

The air dried powdered bark of *T. arjuna* (3.5 Kg) was defatted with Petroleum ether in cold (thrice) at room temperature. The defatted material was then extracted with methanol (three times) overnight at room temperature. The solvent was removed under vacuum at 40° C. and the crude extract so obtained was dissolved in water and extracted with dichloroethane. The dichloroethane extract was washed with water and dried over $Na_2SO_4$. The solvent was removed completely under vacuum at 40° C. and the crude so obtained was subjected to Vacuum Liquid Chromatographic separation, which resulted in the isolation of arjunic acid in 0.04% yield.

EXAMPLE-5

The air dried powdered bark of *T. arjuna* (1.5 Kg) was defatted with Petroleum ether in cold (thrice) at room temperature. The defatted material was then extracted with acetone (three times) overnight at room temperature. The solvent was removed under vacuum at 40° C. and the crude extract so obtained was dissolved in water and extracted with $CHCl_3$. The $CHCl_3$ extract was washed with water and dried over $Na_2SO_4$. The solvent was removed completely under vacuum at 40° C. and the crude so obtained was subjected to column chromatographic separation, which resulted in the isolation of arjunic acid in 0.03% yield.

EXAMPLE-6

The air dried powdered bark of *T. arjuna* (2.5 Kg) was defatted with $CH_2Cl_2$ in cold thrice at room temperature. The defatted material was then extracted with ethanol three times overnight at room temperature. The solvent was removed under vacuum at 40° C. and the crude extract so obtained was dissolved in water and extracted with diethyl ether. The diethyl ether extract was washed with water and dried over $Na_2SO_4$. The solvent was removed completely under vacuum at 40° C. and the crude so obtained was subjected to Column Chromatographic separation, which resulted in the isolation of pure arjunic acid in 0.025% yield.

EXAMPLE-7

Column Chromatography of Diethyl Ether Extract

Activity guided fractionation led us to work on a diethyl ether soluble fraction for isolation of compounds. The diethyl ether soluble crude extract (100 g) was column chromatographed (CC) over silica gel (1.5 Kg) using varying concentrations of eluant ethyl acetate in hexane, in the ratio of 98:2, 95:5, 90:10, 85:15, 80:20, 75:25, 70:30, 60:40, 50:50, 40:60, 30:70, 20:80, 10:90, 100. The volumes of fraction collected were 100 ml each and were monitored through TLC. The thin layer chromatography (TLC) was carried out on silica gel $_{60}F_{254}$ readymade plates of thickness 0.25 mm. For visualization spots on TLC plates were at first exposed to UV light (254 & 366 nm, CAMAG UV lamps) and then to iodine vapour. Finally, the plates were sprayed with vanillin-ethanol-sulphuric acid reagent (1 g: 95 ml: 5 ml) followed by heating for 15 min at 110° C. The fractions giving similar spots were combined. In this manner, we were able to isolate seven compounds which have been assigned as: substance A, substance B, substance C, substance D, substance E, substance F and substance G, addressing $^2$-sitosterol, arjunic acid, arjunolic acid, $^2$-sitosterol-$^2$-D-glucoside, arjungenin, arjunetin and arjunglucoside-I, respectively.

TABLE 1

Compounds isolated from the diethyl ether fraction of ethanolic extract of bark of *Terminalia arjuna*

| Sl. No. | Compound | Molecular Formula | Melting Point | Identified as | Yield* % |
|---|---|---|---|---|---|
| 1 | Substance B | $C_{30}H_{48}O_5$ | >280° C. (decompose | Arjunic Acid | 0.004 |
| 2 | Substance E | $C_{30}H_{48}O_6$ | 293-294° C. | Arjungenin | 0.007 |
| 3 | Substance F | $C_{36}H_{58}O_{10}$ | 232-234° C. | Arjunetin | 0.002 |
| 4 | Substance G | $C_{36}H_{58}O_{11}$ | 232-233° C. | Arjun-glucoside-I | 0.001 |

*Based on dry weight of the plant material.

EXAMPLE-8

Preparative HPLC of Fractions of Diethyl Ether Extract

Fraction no. 1810-2040 eluted with hexane:ethyl acetate in the ratio 5:95 by column chromatography of the diethyl ether extract were collected and monitored by TLC, which showed mixture of compounds with one major constituent. Thus, for purification of the major compound, the fractions were subjected to preparative HPLC, which yielded substance G as crystalline compound. Chromatographic conditions performed for preparative HPLC were: mobile phase, methanol: $H_2O$ (50:50)); flow rate, 17 ml/min; >>–220 nm; column temperature 26° C., respectively. HPLC used was LC-8A Shimadzu semipreparative equipment.

EXAMPLE-9

Identification of Pure Compounds

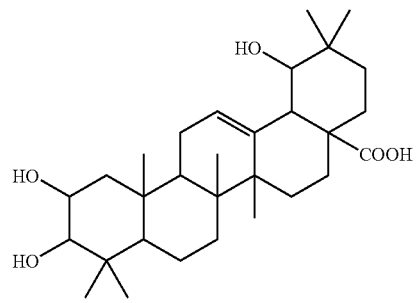

Compound 1, was identified as arjunic acid on the basis of spectral analysis [Row L R, Murthy P S, Subba Rao G S R, Sastry C S P, Rao K V J. *Ind J Chem* 1970; 8:716; Anjaneyulu A S R, Rama Prasad A V. *Phytochemistry* 1982; 21(8):2057], by using hexane-ethyl acetate as eluent in the ratio (50:50/v:v) and crystallized by using methanol.

Compound 2, was identified as arjungenin by spectral analysis [Honda T, Murae T, Tsuyuki T, Takahashi T, Sawai M. *Chem Soc (Japan)* 1976; 49:3213; Anjaneyulu A S R, Rama Prasad A V. *Ind J Chem* 1982; 21B:530], by using hexane-ethyl acetate as eluent in the ratio (50:50/v:v) and crystallized by using methanol.

Compound 3, was identified as arjunetin by spectral analysis [Tsuyuki T, Hamada Y, Honda T, Takahashi T, Matsushita K. *Bull Chem Soc (Japan)* 1979; 52:3127], by using hexane-ethyl acetate as eluent in the ratio (20:80/v:v) and crystallized by using methanol.

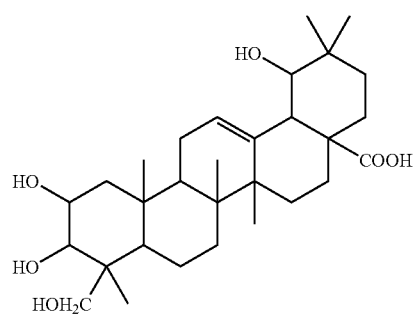

-continued

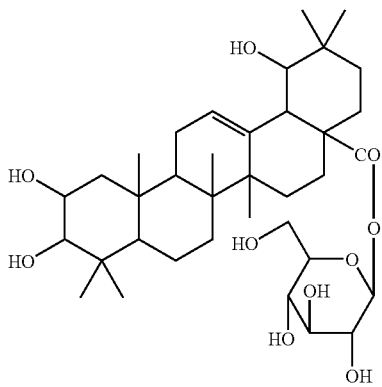

3

EXAMPLE-10

In-Vitro Anticancer MTT Assay

The following six human cancer cell lines were procured from the Cell Repository of the National Center for Cell Sciences (NCCS) at Pune. Their corresponding ATCC No. and the organ from which they were isolated are also mentioned in the table described below:

Cytotoxicity testing in vitro was done by the method of (Woerdenbag et al., 1993; *J. Nat. Prod.* 56 (6): 849-856). $2 \times 10^3$ cells/well were incubated in the 5% $CO_2$ incubator for 24 h to enable them to adhere properly to the 96 well polystyrene microplate (Grenier, Germany). Test compounds dissolved in 100% DMSO in at least five doses were added and left for 6 h after which the compound plus media was replaced with fresh media and the cells were incubated for another 48 h in the $CO_2$ incubator at 37° C. The concentration of DMSO used in our experiments never exceeded 1.25%, which was found to be non-toxic to cells.

| Cancer Cell Line | Source organ | Type | ATCC. No |
|---|---|---|---|
| COLO-320DM | Colon cancer | Suspension | CCL-220 |
| KB-403 | Ovary cancer | Adherent | CCL-17 |
| WRL-68 | Liver cancer | Adherent | CL-48 |
| PA-1 | Ovary cancer | Adherent | CRL-1572 |
| MCF-7 | Breast cancer | Adherent | HTB-22 |
| CaCO2 | Colon cancer | Adherent | — |

Then, 10 µl MTT [3-(4,5-dimethylthiazol-2-yl)-2,5-diphenyltetrazolium bromide; Sigma M 2128] was added, and plates were incubated at 37° C. for 4 h. 100 µl dimethyl sulfoxide (DMSO, Merck, Germany) were added to all wells and mixed thoroughly to dissolve the dark blue crystals. After a few minutes at room temperature to ensure that all crystals were dissolved, the plates were read on a SpectraMax 190 Microplate Elisa reader (Molecular Devices Inc., USA), at 570 nm. Plates were normally read within 1 h of adding the DMSO. The experiment was done in triplicate and the inhibitory concentration (IC) values were calculated as follows: % inhibition=[1-OD (570 nm) of sample well/OD (570 nm) of control well]×100. $IC_{90}$ is the concentration µg/ml required for 90% inhibition of cell growth as compared to that of untreated control. The results are presented in Table-2 indicate that arjunic acid is highly active against colon adenocarcinoma (Caco-2) cell line with 4.5 µg/ml as the $IC_{90}$. It was also found to be active against breast adenocarcinoma, liver and ovarian cancer cell lines at 20-60 µg/ml.

| Compound | Inhibitory Concentration ($IC_{90}$) in µg/ml. | | | | |
|---|---|---|---|---|---|
| | MCF-7 | KB-403 | WRL-68 | Caco-2 | PA-1 |
| Arjunic acid | 50 | — | 20 | 4.5 | 60 |
| Arjungenin | >50 | — | — | 50 | 60 |
| Arjunetin | 50 | — | 20 | 10 | — |
| Arjunglucoside-I | — | — | — | >50 | >50 |

$IC_{90}$: Concentration required to inhibit 90% of cell growth as compared to that of control.

EXAMPLE-11

Derivatives of Arjunic Acid, which can be Used as Anticancer

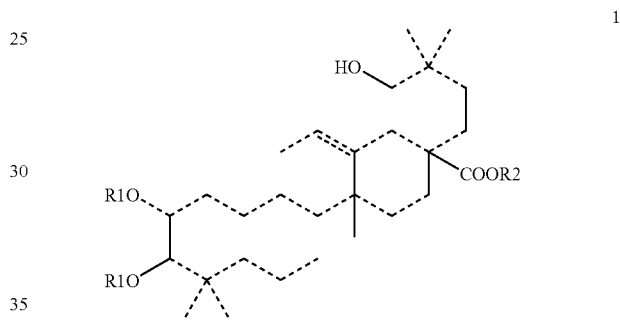

1

| Compounds | R1 | R2 |
|---|---|---|
| Arjunic acid | H | H |
| Arjunic acid methyl ester | H | $CH_3$ |
| 2,3-Di-O-acetyl arjunic acid | Acetate | H |
| 2,3-Di-O-acetyl arjunic acid methyl ester | Acetate | $CH_3$ |
| 2,3-Di-O-ethyl arjunic acid methyl ester | $C_2H_5$ | $CH_3$ |
| 2,3-Di-O-benzoyl arjunic acid methyl ester | Benzoate | $CH_3$ |
| 2,3-Di-O-(o)-anisoyl arjunic acid methyl ester | o-anisoate | $CH_3$ |
| 2,3-Di-O-(m)-anisoyl arjunic acid methyl ester | m-anisoate | $CH_3$ |
| 2,3-Di-O-(p)-anisoyl arjunic acid methyl ester | p-anisoate | $CH_3$ |
| 2,3-Di-O-crotonoyl arjunic acid methyl ester | Crotonoate | $CH_3$ |
| 2,3-Di-O-palmitoyl arjunic acid methyl ester | Palmitate | $CH_3$ |
| 2,3-Di-O-myristoyl arjunic acid methyl ester | Myristate | $CH_3$ |
| 2,3-Di-O-cinnamoyl arjunic acid methyl ester | cinnamate | $CH_3$ |

ADVANTAGES

1. The main advantage of our process is that it completely omits the use of highly tedious, time taking and expensive column chromatographic purification process used in prior art processes.

2. The other major advantage of our process is that it gives 2-10 times more yield than the all earlier repeated processes.

3. The present process uses simple extraction and purification process for the isolation if arjunic acid, which is easy, less time taking and economical.

We claim:

1. An improved process for the isolation of arjunic acid from the bark of *Terminalia arjuna* which comprises the steps of:

a). drying and grinding the *Terminalia arjuna* bark;

b). defattening the *Terminalia arjuna* bark in a first organic solvent selected from the group consisting of petroleum spirit, hexane, benzene, toluene, and dichloromethane;

c). extracting the defattened bark with a polar second organic solvent, at a temperature in the range of 20-40° C. and removing the polar second organic solvent, under vacuum, at a temperature in the range of 35-45° C. to obtain a crude arjunic acid rich fraction;

d). dissolving the above said crude arjunic acid rich fraction in water and further extracting it with a third organic solvent selected from the group consisting of dichloromethane, dichloroethane, chloroform, ethyl acetate, and diethyl ether followed by;

e). washing the resultant fraction obtained in step d). with water, drying it and removing the third organic solvent, under vacuum at a temperature in the range of from 35 to 45° C.; and f). subjecting the fraction from step e). to Vacuum Liquid Chromatography (VLC) followed by;

g). gradient elution of the VLC column with mixtures of at least two solvents thereby yielding the compound arjunic acid.

2. An improved process according to claim 1 wherein the extraction of *Terminalia arjuna* bark in step c). is done at least three times with said polar second organic solvent.

3. An improved process according to claim 1 wherein said polar second organic solvent used for the extraction of defattened *Terminalia arjuna* bark is selected from the group consisting of dichloromethane, chloroform, ethyl acetate, ether, acetone, methanol, and ethanol.

4. An improved process according to claim 3 wherein said polar second organic solvent used to extract the defattened bark is methanol.

5. An improved process according to claim 1 wherein said third organic solvent used for step d). is dichloroethane.

6. An improved process according to 1, wherein the gradient elution of the vacuum liquid chromatography (VLC) column is carried out by mixtures of a first solvent and second solvent in various proportions in increasing order of polarity, wherein said first solvent is selected from the group consisting of dichloromethane, dichloroethane, chloroform, ethyl acetate, and diethyl ether and wherein said second solvent is selected from the group consisting of acetone, methanol, and ethanol.

7. An improved process according to 1, wherein the yield of arjunic acid obtained after step g). is in the range of 0.02-0.04% (W/W).

8. An improved process according to 1, wherein the arjunic acid obtained is a biologically active agent against human cancer disease.

9. An improved process according to 1, wherein the arjunic acid obtained is useful as an anti cancer agent against ovarian (PA-1), colon (Caco-2), breast (MCF-7) and liver (WRL-68) cancer cells.

* * * * *